United States Patent
Sulzbach et al.

[11] Patent Number: 5,990,330
[45] Date of Patent: Nov. 23, 1999

[54] RECOVERY OF HIGHLY FLUORINATED CARBOXYLIC ACIDS FROM THE GAS PHASE

[75] Inventors: Reinhard Albert Sulzbach, Burghausen; Wilhelm Kowatsch, Garching; Dieter Steidl, Hofheim, all of Germany

[73] Assignee: Dyneon GmbH, Germany

[21] Appl. No.: 08/612,388

[22] Filed: Mar. 7, 1996

[30] Foreign Application Priority Data

| Mar. 9, 1995 | [DE] | Germany | 195 08 447 |
| Jul. 26, 1995 | [DE] | Germany | 195 27 276 |

[51] Int. Cl.$^6$ ........................................ C11B 3/00
[52] U.S. Cl. .................. 554/202; 554/175; 554/195; 95/149
[58] Field of Search ................... 554/202, 175, 554/195; 95/149

[56] References Cited

U.S. PATENT DOCUMENTS 2,516,127  7/1950  Laur et al. ........................ 260/450

FOREIGN PATENT DOCUMENTS

| 814839 | 6/1937 | France . |
| 2546320 | 4/1977 | Germany . |
| 2423272 | 5/1983 | Germany . |
| 1127521 | 9/1968 | United Kingdom . |

*Primary Examiner*—Deborah D Carr
*Attorney, Agent, or Firm*—James V. Lilly

[57] ABSTRACT

Highly fluorinated carboxylic acids can be removed from exhaust gas streams by scrubbing with concentrated alkali solutions if these alkali solutions have a density high enough for the salt of the highly fluorinated carboxylic acid to separate out as an independent phase. An apparatus suitable therefor contains a scrubber and a separation vessel which is advantageously equipped with a conveying element, a collection vessel connected via an overflow and a circulation line for the scrubbing liquor.

7 Claims, 1 Drawing Sheet

RECOVERY OF HIGHLY FLUORINATED CARBOXYLIC ACIDS FROM THE GAS PHASE

DESCRIPTION

In the polymerization of fluorinated monomers in aqueous dispersion, highly fluorinated carboxylic acids are used as emulsifiers. Those which are principally used for this are perfluorinated alkanecarboxylic acids having 7 to 10 carbon atoms, in particular perfluorooctanoic acid, in the form of readily soluble salts thereof, preferably ammonium salts.

If the fluoropolymers are obtained by coagulation from the fluoropolymer latex primarily formed, the highly fluorinated carboxylic acids remain to a considerable extent in the fluoropolymer powder formed. Depending on the pH at which the coagulation process is carried out, the highly fluorinated carboxylic acids can be present either as free acids or in the form of their ammonium salts. Mixtures of free acids and ammonium salts are also possible. The ammonium salts of the highly fluorinated carboxylic acids have a considerable vapor pressure at the conventional drying temperatures for fluoropolymer powders in the range between 120 and 300° C., so that they are liberated together with the evaporating water in the air-drying of the powder and are then present, usually in very low concentration, in the exhaust gases or exhaust air of the dryer. Free highly fluorinated carboxylic acids together with water form low-boiling azeotropes, so that substantially quantitative separation from the fluoropolymer powder into the gas phase is possible.

Numerous fluoropolymers are currently prepared on an industrial scale by the emulsion polymerization process. These include: emulsion polymers of tetrafluoroethylene, which can be modified with small amounts of hexafluoropropylene and/or perfluoropropyl vinyl ether and which, as so-called paste products, cannot be processed from the melt, copolymers of tetrafluoroethylene and hexafluoropropylene or perfluoropropyl vinyl ether, copolymers of tetrafluoroethylene, ethylene and, if appropriate, other comonomers, and copolymers of vinylidene fluoride with other comonomers such as tetrafluoroethylene and hexafluoropropylene, to name only the essential examples.

The process according to the invention can be used in the work up of all of these fluoropolymers. Seen quite generally, the process according to the invention is always applicable when highly fluorinated alkanecarboxylic acids are present in exhaust air or exhaust gas streams and are to be separated off from these. It is also readily applicable when highly fluorinated carboxylic acids are present in very low concentration.

Highly fluorinated carboxylic acids, on the one hand, are expensive substances and, on the other hand, are not biodegradable, so that for reasons of costs and environmental protection they must be recovered as quantitatively as possible.

The elimination of highly fluorinated carboxylic acids from exhaust gases or exhaust air by scrubbing out with water is unsatisfactory, since in the case of the free acids, because of the high vapor pressure, there is not a sufficiently good purification, and thus the efficiency of the scrubbing process is insufficient. In the case of the ammonium salts, even at relatively low enrichment, precipitation of ammonium salts is experienced in the scrubbing solution, which makes concentration to higher contents more difficult.

The removal of the highly fluorinated carboxylic acids from exhaust gases by scrubbing out with diluted alkali solutions in practice likewise encounters great difficulties, since the acids and particularly their salts, as highly surface-active substances, lead in this case to strong foam formation. The industrial recovery of these valuable substances in this manner is therefore likewise made much more difficult. The addition of conventional defoamers does not solve these difficulties.

It has now been found that highly fluorinated carboxylic acids or their ammonium salts can readily be scrubbed out of exhaust gas streams if an alkaline scrubbing solution of high density is used, more precisely if either concentrated alkali solutions are used or salts, preferably alkali metal salts, are added to the more dilute alkali solutions. This suppresses the foaming. Moreover, the solubility of the salts formed of the highly fluorinated. carboxylic acids in the scrubbing medium is greatly decreased so that the salts of the fluorocarboxylic acids separate out in concentrated form as a second phase from the alkaline scrubbing medium and thus can be easily separated off from the alkaline scrubbing medium.

It is of no importance for the process according to the invention whether the highly fluorinated carboxylic acids are present in free form or in the form of ammonium salts thereof in the exhaust gases to be cleaned, since the ammonium salts are likewise converted into the corresponding alkali metal salts in the alkaline scrubbing solution.

The temperature of the scrubbing process is not critical. It can be about 10 to 80° C., preferably 20 to 50° C. At lower temperatures, the solubility limits of alkali solution and alkali metal salt must be heeded. The scrubbing solution as such is to be a true solution. The alkali solution or the alkali metal salt must not crystallize out.

The novel process can be operated either at a pressure below 1 bar absolute, at atmospheric pressure or at a gauge pressure of a plurality of bars.

In a preferred embodiment, the density of the alkaline scrubbing solution is set to a value which is higher than the density of the precipitating salts of fluorocarboxylic acids, so that these separate out as an upper phase on the high-density scrubbing solution in a settling tank and are ejected. The scrubbing solution is taken off at the bottom and returned directly to the scrubbing process. The density of the alkaline scrubbing solution is to be above 1.15 g/cm$^3$, preferably above 1.3 g/cm$^3$, at the appropriate temperature in the scrubber. The circulated scrubbing solution contains less than 1%, generally less than 0.1%, of salts of the highly fluorinated carboxylic acids, here and in the following the percentages being by weight.

Interfering foam formation does not occur in the scrubbing process under these conditions. The salts of the highly fluorinated carboxylic acids precipitating out do not interfere with the scrubbing process, since they are separated off in a separation vessel immediately after their formation.

Expediently, the alkaline compound selected is an alkali metal hydroxide, preferably potassium hydroxide solution and in particular sodium hydroxide solution, the concentration being such that the density is above 1.15 g/cm$^3$. With potassium hydroxide solution, this is the case at a concentration of above 16% and with sodium hydroxide solution this is the case at a concentration of above 14%. Mixtures of different alkalis are also possible.

If it is wished to employ lower concentrations of alkali metal hydroxide, the scrubbing solution density of >1.15 g/cm$^3$ can also be achieved by addition of a salt. Salts which are suitable are quite generally inorganic compounds which do not form sparingly soluble hydroxides in the alkaline environment. These are, in particular, alkali metal salts such as sodium or potassium chloride, bromide or sulfate. However, since chloride ions can cause corrosion when metals are used as material for the work-up equipment, other salts, such as sulfates, are preferred to set the density of the scrubbing solution. Advantageously, a salt is selected having the same cation as the alkaline compound, when sodium hydroxide solution is used, therefore, preferably sodium sulfate. Mixtures of salts are also possible.

The lighter, upper phase containing the salts of the highly fluorinated carboxylic acids occurs in the form of a salt paste to which alkaline aqueous medium, that is alkali metal hydroxide and, if appropriate, also the added salt, still adheres.

When perfluorooctanoic acid is recovered, in the case of the preferred use of sodium hydroxide solution, the upper phase containing valuable material comprises:

about 5 to about 20% of sodium salt of perfluorooctanoic acid, less than 10% of sodium hydroxide and water, to make up 100%.

When sodium hydroxide solution and sodium sulfate are used, the upper phase containing the valuable material comprises:

about 30 to about 55% of sodium salt of perfluorooctanoic acid, less than 10%, preferably less than 5%, of sodium hydroxide, about 20 to 40% of sodium sulfate and water, to make up 100%.

In the upper phase containing valuable material, sodium carbonate can also additionally be present if the exhaust gas stream to be cleaned contains carbon dioxide.

These compositions given here are to be taken as being exemplary. They are influenced by the given concentration of alkali metal hydroxide and by the concentration of the added salt in the scrubbing solution.

If the upper phase which has separated out is collected, for example in a tank, it is observed, that after standing for several hours, further enrichment of the salts of the highly fluorinated carboxylic acids occurs, by at least two phases forming again. By analysis, it is established in which phase the salts of the highly fluorinated carboxylic acids are contained and the other phases are preferably returned to the process.

Under certain conditions, the enriched salt paste of the highly fluorinated carboxylic acids becomes solid. Those skilled in the art will then decide in the specific case whether, in view of the possibilities open to them in terms of apparatus, a higher or lower concentration of salts of the highly fluorinated carboxylic acids is desirable in the further processing.

Further processing of the salts of the highly fluorinated carboxylic acids to give a salt solution, preferably an ammonium salt solution, reusable in the polymerization of fluoromonomers requires further purification steps. In this case, for example, the esterification process described in U.S. Pat. No. 5,442,097 can be employed.

BRIEF DESCRIPTION OF THE DRAWINGS

For further explanation of the process according to the invention, a continuous recovery of perfluorooctanoic acid is explained in more detail with reference to FIG. 1.

An essential component of the system is the scrubber 1 in which the perfluorooctanoic-acid-containing exhaust air is brought into intimate contact via the line 2 with the high-density alkaline scrubbing solution, fed through the line 3. Thereby, the alkali metal salt of the perfluorooctanoic acid forms which is sparingly soluble in the alkaline scrubbing solution and is separated out as a solid phase. The heterogeneous mixture of alkaline scrubbing solution and separated alkali metal salt of perfluorooctanoic acid flows via the line 4 into the separation vessel 5. Here, in a calm zone of the vessel, the salt of perfluorooctanoic acid of lower specific gravity separates off in the form of a salt paste as an upper phase from the denser alkaline scrubbing solution. The salt paste formed is discharged via an overflow 6 at the vessel, together with the adhering alkaline scrubbing solution, via the line 7 and runs off continuously into a collection vessel 8. The discharge of the salt paste can be promoted by a conveying element 9, for example a very slowly running stirrer. The height of the stirrer 9 is set in this case so that it is just immersed in the vessel contents and by this means does not interfere with the separation process in the vessel.

Figure 1:
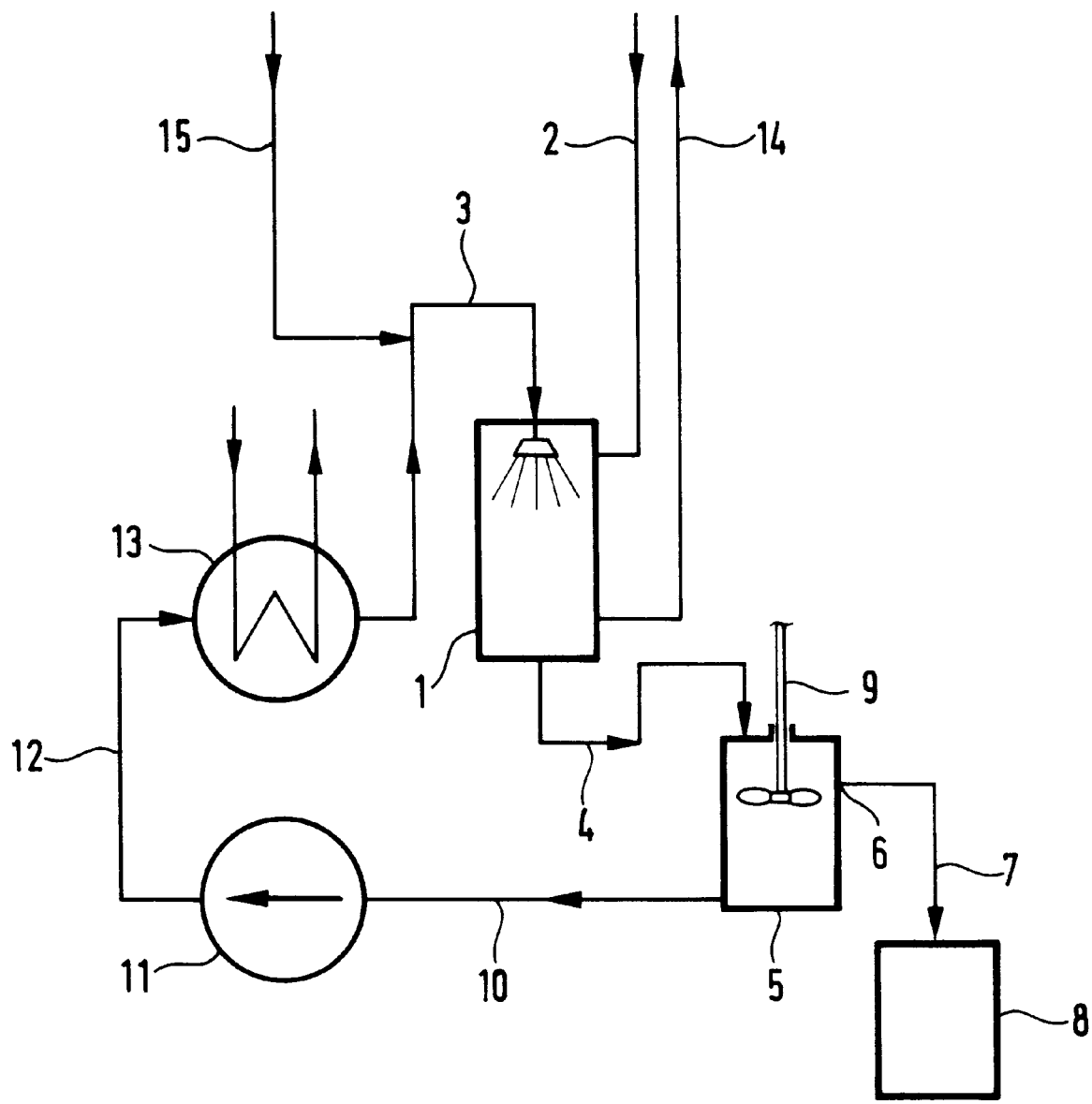

In a preferred embodiment, the crude salt of the perfluorooctanoic acid separated off as upper phase in the collection vessel 8 is admixed with 1 part by weight of water per 2 to 5 parts by weight of salt, mixed intimately and the phases formed are separated again.

The high-density alkaline scrubbing solution is recycled from the lower part of the separation vessel 5 via the line 10 by the pump 11, via the line 12 through a heat exchanger 13 and the line 3, to the scrubbing column 1. The cleaned exhaust air is led off via the line 14. The circulated scrubbing solution no longer contains significant amounts of alkali metal salt of perfluorooctanoic acid owing to its low solubility. The alkaline scrubbing solution is supplemented via the line 15 with alkali solution and, if appropriate, with salt to an extent corresponding to the discharge of these components at the overflow of the vessel 5. This maintains the high scrubbing solution density required. The scrubbing solution components can be replenished continuously or by portions.

Furthermore, the water balance must be taken into account: water vapor is generally introduced into the scrubber 1 together with the perfluorooctanoic-acid-containing exhaust gases which originate from drying processes. In this case, the vapors condense in the high-density scrubbing medium and decrease the concentration. On the other hand, the cleaned exhaust air which leaves the scrubber 1 is saturated with water and some water is discharged via the vessel 5. In order to maintain the concentration of the scrubbing medium it is advisable to measure the density continuously and according to this to replenish alkali solution, if appropriate salt and water, in the required amounts.

The cleaned exhaust air escaping from the scrubber 1 only contains very low amounts of perfluorooctanoic acid or ammonium salt of perfluorooctanoic acid. Values are achieved which are below 5 mg/m$^3$ (S.T.P.), preferably below 1 mg/m$^3$ (S.T.P.), of exhaust gas.

The invention is now described in more detail on the basis of the following examples. Here also, the percentages are by weight.

EXAMPLE 1

400 m$^3$ (S.T.P.)/h of exhaust air at a temperature of 171° C. from a drying process for fluoropolymer powder are introduced into a commercial scrubbing column having a length of 2000 mm and an inner diameter of 250 mm. The exhaust air contains 750 mg/m$^3$ (S.T.P.), corresponding to 300 g/h, of perfluorooctanoic acid. About 20 kg/h of water are additionally transported with the exhaust air from the dryer into the scrubbing process. The pressure in the scrubbing column is about 1 bar absolute.

10 m$^3$/h of an alkaline scrubbing liquid essentially comprising aqueous sodium hydroxide solution having a density of 1.34 g/cm$^3$ and a temperature of 45° C. are added to the scrubber via a nozzle. At the lower part of the scrubbing column, the cleaned exhaust gas stream of 400 m$^3$ (S.T.P.)/h escapes which only contains 0.8 mg/m$^3$ (S.T.P.), corresponding to 0.32 g/h, of perfluorooctanoic acid. In addition, water vapor is present corresponding to the water partial pressure at the temperature prevailing in the scrubber of about 45° C.

The scrubber is operated in cocurrent flow. The alkaline scrubbing medium and the resulting sodium salt of perfluorooctanoic acid flow out of the column directly into a separation vessel having a volume of 0.4 m$^3$. There, the sodium salt of perfluorooctanoic acid which is insoluble in the alkaline scrubbing solution floats as a pasty layer. The alkaline scrubbing solution which contains virtually no more sodium salt of perfluorooctanoic acid, is taken off from the separation vessel at the bottom and recycled to the scrubbing column by a pump via a heat exchanger. The concentration of dissolved sodium salt of perfluorooctanoic acid in the scrubbing medium is about 20 mg/l. The density of the scrubbing liquid is maintained at the desired value of about 1.34 g/cm$^3$ by addition of sodium hydroxide solution. The sodium salt of perfluorooctanoic acid separated off as a pasty layer runs off at an overflow of the separation vessel together with some scrubbing medium into a tank. The discharge operation is reinforced by a very slowly rotating stirrer which is just immersed in the upper layer.

In the tank, after standing for several hours, two phases again separate out, a lower phase, which essentially comprises excess scrubbing liquid, and a pasty upper phase. The lower phase is separated off and returned to the scrubbing process.

The pasty upper phase containing the sodium salt of perfluorooctanoic acid is subjected to the procedure below to decrease the sodium hydroxide solution content and for improved handling:

addition of 25 kg of water per 100 kg of upper phase with stirring, phase separation after standing for several hours, separating off the lower phase and returning it to the scrubbing process after increasing the concentration with sodium hydroxide solution, further addition of 50 kg of water per 100 kg of upper phase with stirring and sampling with stirring.

The sample obtained in this manner has the following composition:

21.9% sodium perfluorooctanoate 8.9% sodium hydroxide 3.6% sodium carbonate

Remainder water

The concentrate thus obtained is fed to further work up to obtain pure 100% perfluorooctanoic acid.

It may be mentioned that although the concentrate thus obtained is a stirrable and pumpable mixture, it is not a stable solution of the sodium salt of perfluorooctanoic acid. In order to obtain a stable solution, more water would have to be added. However, this is not necessarily required for further work up.

Owing to the described recycling into the scrubbing process of the lower phase separated out, no perfluorooctanoic acid is lost.

EXAMPLE 2

A procedure similar to Example 1 is employed. As a difference, however, the scrubbing solution used is a mixture of 5% sodium hydroxide, 19% sodium sulfate and the remainder essentially water. The amount recirculated is 6 m$^3$/h at 26° C. The density of the scrubbing medium is 1.24 g/cm$^3$. The exhaust gas stream introduced is 400 m$^3$ (S.T.P.)/h. It contains 770 mg/m$^3$ (S.T.P.), corresponding to 308 g/h, of perfluorooctanoic acid. At the lower part of the column, the cleaned exhaust gas stream escapes which still contains 3 mg/m$^3$ (S.T.P.), corresponding to 1.2 g/h, of perfluorooctanoic acid. The phase floating in the separation vessel which contains the sodium salt of perfluorooctanoic acid has the following composition:

34.0% sodium perfluorooctanoate 3.5% sodium hydroxide 20.0% sodium sulfate 2.1% sodium carbonate Remainder water

We claim:

1. A process for the recovery of highly fluorinated carboxylic acids or their ammonium salts from exhaust gas streams, which comprises bringing the exhaust gas into contact with an alkaline scrubbing solution of a concentration such that the salt of the highly fluorinated carboxylic acid separates out as a separate phase.

2. The process as claimed in claim 1, wherein the alkaline scrubbing solution has a density >1.15 g/cm$^3$.

3. The process as claimed in claim 1, wherein the alkaline scrubbing solution has a density >1.3 g/cm$^3$.

4. The process as claimed in claim 1, wherein the alkaline scrubbing solution is an alkali metal hydroxide solution which optionally contains a salt.

5. The process as claimed in claim 4, wherein the salt is an alkali metal salt which contains the same cation as the alkali metal hydroxide.

6. The process as claimed in claim 4, wherein the alkali metal hydroxide solution is sodium hydroxide solution or potassium hydroxide solution.

7. The process as claimed in claim 1, wherein the salt of the highly fluorinated carboxylic acid separates out as an upper phase on the scrubbing solution.

* * * * *